United States Patent [19]

Dickson

[11] 4,306,861
[45] Dec. 22, 1981

[54] SYSTEM FOR RECORDING MANDIBULAR MOTION
[75] Inventor: Athol A. Dickson, Richardson, Tex.
[73] Assignee: Athol Corporation, Richardson, Tex.
[21] Appl. No.: 139,641
[22] Filed: Apr. 14, 1980
[51] Int. Cl.³ .............................................. A61C 19/04
[52] U.S. Cl. ......................................... 433/69; 433/73
[58] Field of Search ........................ 433/73, 68, 69, 71
[56] References Cited
U.S. PATENT DOCUMENTS
3,058,217  10/1962  Joffe ...................................... 433/69
4,026,024  5/1977  Tradowsky ........................... 433/69

Primary Examiner—Robert Peshock
Attorney, Agent, or Firm—Richards, Harris & Medlock

[57] ABSTRACT

An apparatus (10) for recording motion of the mandible relative to the maxilla in reconstructive dentistry comprises a lateral bar (16) attachable to the upper jaw. A pair of stylii (22) are mounted for spring-assisted vertical movement in the bar (16) for cooperation with an underlying tracing plate (36) attachable to the lower jaw. The apparatus (10) can be utilized with patients having dentulous or edentulous mouths. In the preferred embodiment, an adjustable bearing pin assembly (72) is utilized to control minimum spacing between the upper and lower jaws during recordation of the mandibular motion.

9 Claims, 10 Drawing Figures

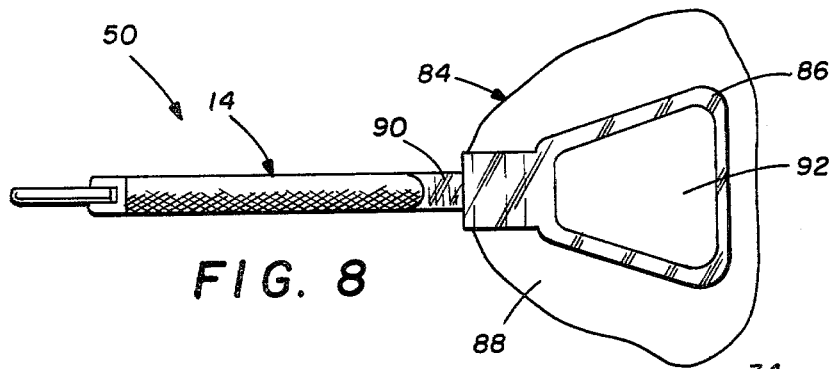
FIG. 8
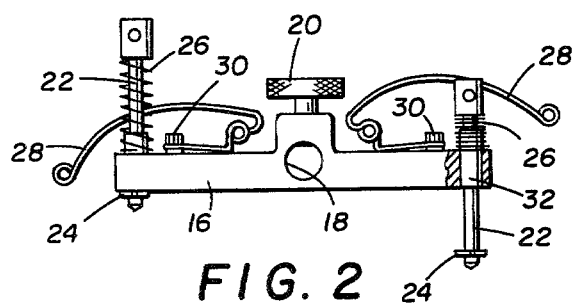
FIG. 2
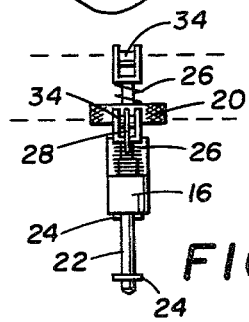
FIG. 3
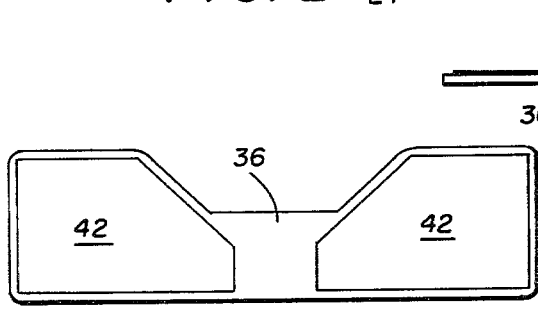
FIG. 5
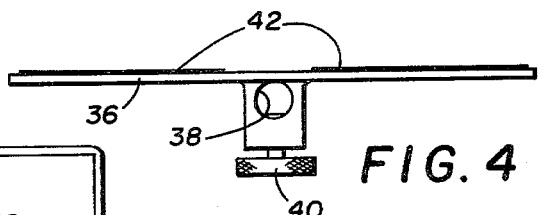
FIG. 4
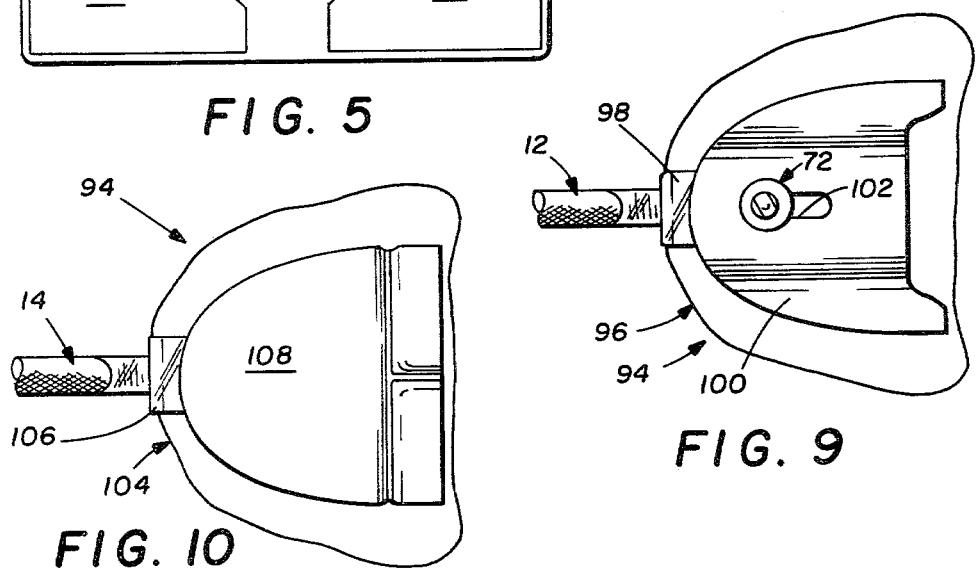
FIG. 10
FIG. 9

SYSTEM FOR RECORDING MANDIBULAR MOTION

TECHNICAL FIELD

This invention relates generally to dental apparatus, and more particularly to a system for recording motion of the mandible for purposes of diagnostic and reconstructive dentistry.

BACKGROUND ART

The lower jaw (mandible) is supported for movement relative to the upper jaw (maxilla) by a pair of temporomandibular joints which interconnect the lower jaw and skull in front of the ears on each side of the head. The temporomandibular joints determine the particular range of motion of the lower jaw and its positional relationship to the upper jaw. Protrusion and lateral excursion of the lower jaw varies from person to person.

In performing reconstructive dentistry, such as fitting a person with full or partial dentures, the particular range of motion of a patient's lower jaw must be taken into account to provide proper clearance for chewing as well as for opening and closing of the mouth without grinding or other unnecessary interference between the teeth. This procedure usually entails taking various measurements of the mandibular motion and then transferring these measurements to a dental articulator like that shown in U.S. Pat. No. 3,624,906 to Granger for reproducing the movements to facilitate adjustment and fitting of the appliances to the patient. Measurement of mandibular motion also can be useful in diagnosing or treating problems associated with the temporomandibular joints.

The mandibular motion recorders of the prior art, however, have not been altogether satisfactory. Some of the prior devices have not been interchangeable between patients having either dentulous (with teeth) or edentulous (without teeth) mouths, or have been interchangeable only with the addition of elaborate accessories. Some devices have not operated completely smoothly but have tended to catch or bind in portions of the movement. Such binding or roughness in action reduces accuracy of the measurement and causes some discomfort to the patient. In addition, the prior devices for recording mandibular motion have tended to be cumbersome and difficult to manipulate, and have suffered from the further disadvantages of undue complexity in construction and therefore expense.

A need has thus arisen for a new and improved apparatus for recording mandibular motion.

DISCLOSURE OF INVENTION

The present invention comprises an apparatus for recording mandibular motion which overcomes the foregoing and other difficulties associated with the prior art. In accordance with the invention, there is provided a system for recording mandibular motion of patients having dentulous or edentulous mouths. The recorded measurements are then utilized with a dental articulator to modify the occlusal surfaces of the dentures as necessary in accordance with the patient's mandibular movement characteristics to achieve a proper fit.

More specifically, the present invention comprises a system for measuring motion of the mandible in diagnostic and reconstructive dentistry procedures. The system includes a T graph with upper and lower portions for connection to the upper and lower jaws, respectively. The upper portion includes a bar with stylii mounted at opposite ends thereof for engagement with tracing panels on the lower portion. Each stylus includes a roller bearing mounted at the upper end thereof and is normally biased upward by a small coil spring. A pair of lever springs are mounted on the stylii bar for selective placement on the roller bearing of each stylus to bias the stylii downward against the tracing panels without binding.

In the case of a patient with a dentulous mouth, the T graph portions are mounted on sleeve bolts attached to a clutch system which enables disengagement of the teeth and thus facilitates control of mandibular motion. In the case of a patient with an edentulous mouth, the T graph portions are mounted on sleeve bolts attached to trays containing molds conforming to the gums of the patient.

In accordance with another aspect of the invention, the system herein utilizes an intraoral bearing pin assembly to control minimum spacing between the upper and lower jaws while recording mandibular motion.

BRIEF DESCRIPTION OF DRAWINGS

A fuller understanding of the invention can be had by referring to the following Detailed Description in conjunction with the accompanying Drawings, wherein:

FIG. 2 is a front view of the upper portion of the T graph;

FIG. 3 is a side view of FIG. 2;

FIG. 4 is a front view of the lower portion of the T graph;

FIG. 5 is a top view of FIG. 4;

FIG. 8 is a top view of the mandibular clutch for use with dentulous mouths;

FIG. 9 is a bottom view of a maxillary tray for use with edentulous mouths; and

FIG. 10 is a top view of a mandibular tray for use with edentulous mouths.

DETAILED DESCRIPTION

Figure 1:
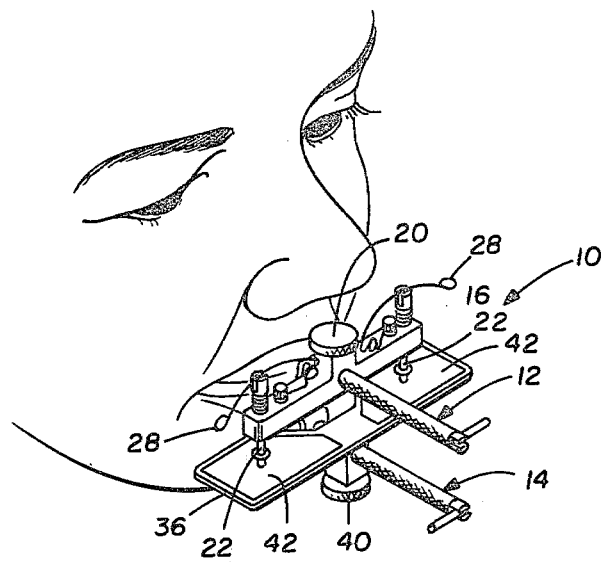
FIG. 1 is a perspective view of a system for recording mandibular motion in accordance with the invention attached to a patient.

Referring now to the Drawings, wherein like reference numerals designate like or corresponding components throughout the views, and particularly referring to FIG. 1, there is shown the system for recording mandibular motion 10 of the invention. System 10 is mounted on a pair of sleeve bolts 12 and 14 protruding from the mouth of the patient. Upper sleeve bolt 12 is attached to the upper jaw (maxilla) while lower sleeve bolt 14 is attached to the lower jaw (mandible) of the patient. As will be more fully explained hereinafter, system 10 includes a T graph assembly which functions to record mandibular motion of the patient for use in fitting the patient with dentures or performing other diagnostic or reconstructive dentistry procedures.

Referring to FIG. 1 together with FIGS. 2 and 3, system 10 includes a stylii bar 16 with a central opening 18 therein for receiving upper sleeve bolt 12. Stylii bar 16 is secured to sleeve bolt 12 in lateral relationship therewith by means of a thumbscrew 20. A stylus 22 is mounted for vertical movement at each end of bar 16. Stylii 22 are captivated to bar 16 by clips 24 and are normally biased in the upward direction by small springs 26. A lever spring 28 is provided for each stylus 22 for manual positioning thereon to lower the stylii into recording positions. Each lever spring 28 is attached to stylii bar 16 at 30.

To facilitate smooth movement of stylii 22 and thereby reduce the possibility of binding or causing any undue discomfort to the patient or interference with recording of the mandibular motion, each stylus is preferably constructed of half-hard brass coated with nickel and is guided relative to bar 16 by a sleeve 32 of stainless steel. More importantly, as is best shown in FIG. 3, each stylus 22 includes a roller bearing 34 at the upper end thereof for transferring downward pressure from springs 28 without applying lateral torque which might otherwise cause the stylii to bind. The axes of rotation of roller bearings 34 are thus generally transverse to stylii 22 as indicated by the dotted lines in FIG. 3. The mounting and actuation of each stylus 22 on stylii bar 16 comprise significant features of the present invention.

Referring to FIG. 1 together with FIGS. 4 and 5, the lower T graph portion of system 10 includes a horizontal plate 36 with a central opening 38 therethrough for receiving lower sleeve bolt 14. Plate 36 is secured in generally lateral relationship with sleeve bolt 14 by means of thumbscrew 40. A pair of tracing panels 42 are attached to the upper surface of plate 36 for cooperation with stylii 22 above to record the mandibular motion.

FIGS. 6-10 illustrate the means by which the T graph of system 10 shown in FIGS. 1-5 can be used with patients having dentulous or edentulous mouths. This comprises another significant feature of the present invention. It will be appreciated that motion of the mandible cannot be accurately measured and recorded without at least some control of the minimum spacing between the upper and lower jaws. In the case of dentulous mouths, the mandible and maxilla must be separated somewhat so that engagement of the teeth does not interfere with or prevent motion of the mandible. On the other hand, the mandibles of edentulous mouths must be prevented from closing to an overclosed position during recording. The central bearing pin assembly of the invention facilitates accurate control of the spacing between the upper and lower jaws while recording motion of the mandible.

Figure 6:
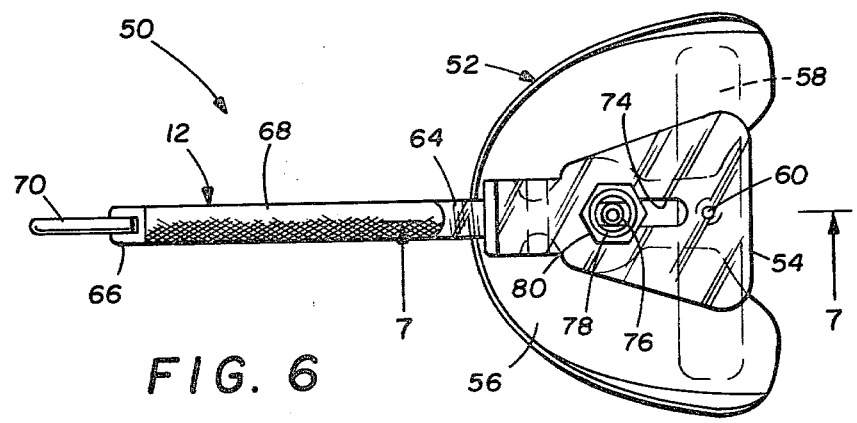
FIG. 6 is a top view of the maxillary clutch for use with dentulous mouths.
Figure 7:
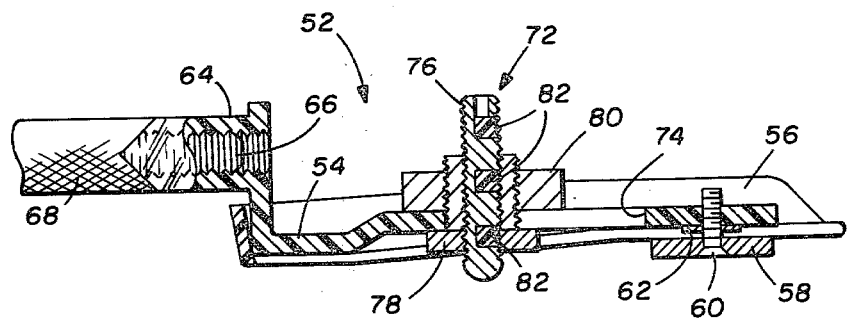
FIG. 7 is an enlarged sectional view taken along lines 7—7 of FIG. 6 in the direction of the arrows.

FIGS. 6, 7 and 8 illustrate clutch system 50 for disengaging the teeth and controlling mandibular motion of patients with dentulous mouths. In particular, FIGS. 6 and 7 show maxillary clutch 52 for attachment to the upper jaw of the patient and for connection to upper sleeve bolt 12. Clutch 52 includes a rigid plate 54 and a flexible tray 56. Tray 56 is secured to plate 54 by a lateral bar 58 and a screw 60 which is preferably captivated to the bar by a clip 62. The inner edges of tray 56 are clamped between plate 54 and bar 58 at the posterior end of the plate. The anterior end of plate 54 includes a threaded fitting 64 for receiving bolt 66 of sleeve bolt 12.

In accordance with the preferred construction, the confronting ends of sleeve 68 of sleeve bolt 12 and fitting 64 are of complimentary V-shaped or other non-circular configuration to provide for self-centering. Bolt 66, which extends through sleeve 68, includes a small pivotal handle 70 at the other end thereof to facilitate attachment and detachment of sleeve bolt 12 to clutch 52.

A central bearing pin assembly 72 is mounted in a longitudinal slot 74 in plate 54 of maxillary clutch 52. As is best shown in FIG. 7, assembly 72 includes an externally threaded pin 76 protruding through an externally threaded housing 78 which is adjustably clamped to plate 54 along slot 74 by nut 80. The lower end of pin 76 is rounded to facilitate travel over the opposing plate (not shown in FIG. 7), while the upper end of the pin is preferably configured to receive an Allen wrench. In accordance with the preferred construction of assembly 72, pin 76 includes one or more nylon plugs 82 embedded therein to prevent undesired rotation within housing 78 as pin 76 contacts the opposing plate during movement of the mandible.

After bearing pin assembly 72 has been covered with a protective material such as blockout clay, dental acrylic is placed into tray 56 to take an impression of the upper teeth with clutch 52. Tray 56, bar 58, screw 60 and the blockout clay are removed after the acrylic has cured. Thus, while recording motion of the mandible, clutch 52 comprises cured acrylic and bearing pin assembly 72 secured to plate 54.

Referring now to FIG. 8, there is shown the mandibular clutch 84 of clutch system 50 after formation of an impression of the lower teeth. Clutch 84 includes an unslotted rigid plate 86 with an impression 88 secured thereto. Plate 86 includes a fitting 90 similar to fitting 64 of clutch 52 for receiving sleeve bolt 14, which is similar in construction to sleeve bolt 12. Before formation of impression 88, clutch 84 includes a flexible tray, bar and screw like clutch 52.

In utilizing clutch system 50, tray 56 of maxillary clutch 52 is first adjusted to the dental arch of the patient before filling with quick cure dental acrylic. Blockout clay is preferably used to protect bearing pin assembly 72 from the acrylic. Clutch 52 is then seated, removed and reseated on the maxillary teeth to form an impression in the acrylic. Tray 56, bar 58, screw 60 and the blockout clay are then removed. After completion of maxillary clutch 52, sleeve bolts 12 and 14 are then secured together in parallel relationship by means of a spacer (not shown) and a similar procedure is followed with clutch 84 to form an impression of the mandibular teeth. A brass plate 92 then is secured to the upper surface of plate 86 for cooperation with bearing pin assembly 72 of maxillary clutch 52 during recording of the mandibular motion.

Referring now to FIGS. 9 and 10, there is shown the clutch system 94 for utilizing the T graph portions of system 10 with patients having edentulous mouths. The maxillary and mandibular portions of clutch system 94 are each formed in conventional manner by means of a wax bite rim, checkbite stone, bite fork and face bow to form a plastic cast or base tray conforming to the gums of the patient. FIG. 9 illustrates the maxillary base tray 96 with a fitting 98 secured to the anterior portion thereof for receiving sleeve bolt 12, and with a brass plate 100 secured to the lower surface thereof. A bearing pin assembly 72 like that described above is mounted in a longitudinal slot 102 in plate 100. FIG. 10 illustrates mandibular base tray 104 with fitting 106 and brass plate 108 secured thereto, the fitting being for receiving lower sleeve bolt 14 and the plate being for cooperation with bearing pin 72 on maxillary tray 100.

From the foregoing, it will be apparent that the present invention comprises an improved mandible motion recording system having several advantages over the prior art. The system herein can be utilized with patients having dentulous or edentulous mouths. The central bearing pin assembly controls minimum spacing between the upper and lower jaws as motion of the mandible is being recorded smoothly and without snags that could cause inaccuracies or discomfort to the patient. Other advantages will suggest themselves to those skilled in the art.

Although preferred embodiments of the invention have been illustrated in the accompanying Drawings and described in the foregoing Detailed Description, it will be understood that the invention is not limited to the embodiments disclosed, but is intended to embrace any equivalents, modifications and rearrangements of elements falling within the spirit and scope of the invention as defined by the following Claims.

I claim:

1. Apparatus for recording motion of the mandible relative to the maxilla, comprising:
    an intraoral upper plate adapted for engagement with the maxilla;
    an upper rod connected at one end to said upper plate and extending extraorally therefrom;
    an intraoral lower plate adapted for engagement with the mandible;
    a lower rod connected at one end to said lower plate and extending extraorally therefrom;
    a bar mounted on said upper rod;
    a pair of guide sleeves mounted at opposite ends of the bar and formed from a first predetermined material;
    a plate mounted on said lower rod beneath said bar;
    a pair of stylii formed from a second predetermined material and each mounted in one of the guide sleeves for vertical movement relative to said bar;
    said first predetermined material of said guide sleeves and said second predetermined material of said stylii comprising bearing means supporting said stylii for reciprocation in said guide sleeves without interference;
    a roller bearing mounted at the upper end of each of the stylii;
    a pair of coil springs each surrounding one of said stylii for biasing each of said stylii upward; and
    a pair of cantilever springs mounted on the bar for selective engagement with the roller bearings of said stylii to bias each of said stylii downward against the action of the coil springs and into engagement with said plate to effect recording of mandibular motion, said engagement of the cantilever springs with the roller bearings preventing binding of the stylii in the guide sleeves.

2. The apparatus of claim 1, further including:
    a pair of tracing panels removably attached to said plate to record movement of said stylii thereover.

3. The apparatus of claim 1, wherein said bar includes an opening for receiving said upper rod, and further including:
    a thumbscrew extending into the opening of said bar for securing said bar to said upper rod.

4. The apparatus of claim 1, wherein said plate includes an opening for receiving said lower rod, and further including:
    a thumbscrew associated with the opening of said plate for securing said plate to said lower rod.

5. The apparatus of claim 1, further including:
    bearing pin means mounted in said upper plate for controlling minimum spacing between the mandible and maxilla during recordation of mandibular motion.

6. A system for recording motion of the mandible relative to the maxilla, comprising:
    an intraoral upper plate;
    an upper rod connected at one end to said upper plate and extending extraorally therefrom;
    an intraoral lower plate;
    a lower rod connected at one end to said lower plate and extending extraorally therefrom;
    bearing pin means mounted in said upper plate for controlling minimum spacing between the maxilla and mandible;
    means secured to said upper and lower rods for recording the mandibular motion;
    tray means for receiving a quantity of dental impression forming material:
    said tray means having an arch shape; and
    means for detachably securing the tray means to intraoral upper plate with the arch of the tray means surrounding the bearing pin means so that a dental impression formed by means of dental impression material received in the tray means is secured to the intraoral upper plate and surrounds the bearing means.

7. The system of claim 6, wherein said bearing pin means comprises:
    a housing mounted on said upper plate;
    an externally threaded post with a generally rounded end extending through said housing; and
    a plurality of semi-rigid inserts extending substantially radially into said post at longitudinally spaced locations therealong for resisting relative rotation between said housing and post.

8. The apparatus for recording motion of the mandible relative to the maxilla according to claim 6 further including:
    a bar mounted on said upper rod;
    a pair of guide sleeves mounted at opposite ends of the bar and formed from a first predetermined material;
    a plate mounted on said lower rod beneath said bar;
    a pair of stylii formed from a second predetermined material and each mounted in one of the guide sleeves for vertical movement relative to said bar;
    said first predetermined material of said guide sleeves and said second predetermined material of said stylii comprising bearing means supporting said stylii for reciprocation in said guide sleeves without interference;
    a roller bearing mounted at the upper end of each of the stylii;
    a pair of coil springs each surrounding one of said stylii for biasing each of said stylii upward; and a pair of cantilever springs mounted on the bar for selective engagement with the roller bearings of said stylii to bias each of said stylii downward against the action of the coil springs and into engagement with said plate to effect recording of mandibular motion, said engagement of the cantilever springs with the roller bearings preventing binding of the stylii in the guide sleeves.

9. A system for recording motion of the mandible relative to the maxilla, comprising:
    an intraoral upper plate;

an upper rod connected at one end to said upper plate and extending extraorally therefrom;

an intraoral lower plate;

a lower rod connected at one end to said lower plate and extending extraorally therefrom;

bearing pin means mounted in said upper plate for controlling minimum spacing between the maxilla and mandible;

means secured to said upper and lower rods for recording the mandibular motion;

tray means for receiving a quantity of dental impression forming material;

said tray means having an arch shape; and means for detachably securing the tray means to intraoral upper plate with the arch of the tray means surrounding the bearing pin means so that a dental impression formed by means of dental impression material received in the tray means is secured to the intraoral upper plate and surrounds the bearing means;

a plate mounted on said lower rod beneath said guide sleeves;

a pair of stylii formed from a second predetermined material and each mounted in one of the guide sleeves for vertical movement relative to said plate;

said first predetermined material of said guide sleeves and said second predetermined material of said stylii comprising bearing means supporting said stylii for reciprocation in said guide sleeves without interference;

a roller bearing mounted at the upper end of each of the stylii;

a pair of coil springs each surrounding one of said stylii for biasing each of said stylii upward; and a pair of cantilever springs mounted on the bar for selective engagement with the roller bearings of said stylii to bias each of said stylii downward against the action of the coil springs and into engagement with said plate to effect recording of mandibular motion, said engagement of the cantilever springs with the roller bearings preventing binding of the stylii in the guide sleeves.

* * * * *